(12) United States Patent
Rich

(10) Patent No.: US 12,336,722 B2
(45) Date of Patent: Jun. 24, 2025

(54) SURGICAL VIEWING SYSTEM

(71) Applicant: Eclipse Orthopaedics, LLC, Warsaw, IN (US)

(72) Inventor: David B. Rich, Warsaw, IN (US)

(73) Assignee: Eclipse Orthopaedics, LLC, Warsaw, IN (US)

(*) Notice: Subject to any disclaimer, the term of this patent is extended or adjusted under 35 U.S.C. 154(b) by 392 days.

(21) Appl. No.: 17/854,580

(22) Filed: Jun. 30, 2022

(65) Prior Publication Data

US 2023/0000501 A1 Jan. 5, 2023

Related U.S. Application Data

(60) Provisional application No. 63/217,556, filed on Jul. 1, 2021.

(51) Int. Cl.
*A61B 17/17* (2006.01)
*A61B 6/00* (2024.01)
*A61B 90/00* (2016.01)

(52) U.S. Cl.
CPC ........ *A61B 17/1703* (2013.01); *A61B 6/4476* (2013.01); *A61B 2090/376* (2016.02)

(58) Field of Classification Search
CPC ..... A61B 6/4423; A61B 8/4272; A61B 8/428; A61B 2090/376; A61B 90/03; A61M 2205/051

See application file for complete search history.

(56) References Cited

U.S. PATENT DOCUMENTS

| 9,782,183 | B1 | 10/2017 | Rich | |
|---|---|---|---|---|
| 2011/0170666 | A1* | 7/2011 | Chen | G01N 23/20008 378/82 |
| 2013/0022175 | A1* | 1/2013 | Abramovich | A61B 6/512 378/189 |
| 2017/0164958 | A1* | 6/2017 | Rich | A61B 17/1615 |
| 2021/0236069 | A1* | 8/2021 | Kotian | A61B 6/102 |

OTHER PUBLICATIONS

Extended European Search Report dated Nov. 3, 2022 for European Patent Application No. 22181835.4 (7 pages).

* cited by examiner

*Primary Examiner* — Keith M Raymond
*Assistant Examiner* — Milton Truong
(74) *Attorney, Agent, or Firm* — TAYLOR & EDELSTEIN, PC

(57) ABSTRACT

A surgical viewing system including an X-ray source, a surgical tool and an actuator. The X-ray source creates a beam of radiation used in an image creating process. The surgical tool has the X-ray source coupled thereto, and the surgical tool has an axis of rotation. The actuator is coupled to the surgical tool causing the beam of radiation to be shifted relative to the axis of rotation.

20 Claims, 6 Drawing Sheets

SURGICAL VIEWING SYSTEM

CROSS REFERENCE TO RELATED APPLICATIONS

This is a non-provisional patent application based upon U.S. provisional patent application Ser. No. 63/217,556, entitled "SURGICAL VIEWING SYSTEM", filed, Jul. 1, 2021, which is incorporated herein by reference.

BACKGROUND OF THE INVENTION

1. Field of the Invention

The present invention relates to a surgical viewing system, and, more particularly, to a surgical viewing system coupled to a surgical tool.

2. Description of the Related Art

Currently there are methods and devices that are used to assist the professional during the installation of an intramedullary nail, or drilling of a hole. An intramedullary nail is designed to be inserted through the center of a bone and affixed to the bone via screws that are installed through the bone. Prior art methods are ineffective in providing a three dimensional, or quasi-three dimensional view of where the bit will drill. An incorrectly drilled hole during surgery results in longer surgery, higher potential for infection, and other trauma that can cause post-op complications.

What is needed in the art is an easy to operate surgical viewing system that improves the ability to perceive where a drilling motion takes place relative to an X-ray source.

SUMMARY OF THE INVENTION

The present invention provides a system that shifts the X-ray source to improve the visual perception of the drill bit to the surgeon.

The invention in one form is directed to a surgical viewing system including an X-ray source, a surgical tool and an actuator. The X-ray source creates a beam of radiation used in an image creating process. The surgical tool has the X-ray source coupled thereto, and the surgical tool has an axis of rotation. The actuator is coupled to the surgical tool causing the beam of radiation to be shifted relative to the axis of rotation.

The invention in yet another form is directed to a surgical tool including a housing, and an X-ray source positioned within the housing. The X-ray source creating a beam of radiation used in an image creating process. The surgical tool having an axis of rotation and an actuator coupled to the surgical tool causing the beam of radiation to be shifted relative to the axis of rotation.

An advantage of the present invention is that the surgeon using the invention can get an improved perception of the placement of the bit of the drill.

Another advantage of the present invention is that the imaging control and shifting of the radiation source is controlled with one hand.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
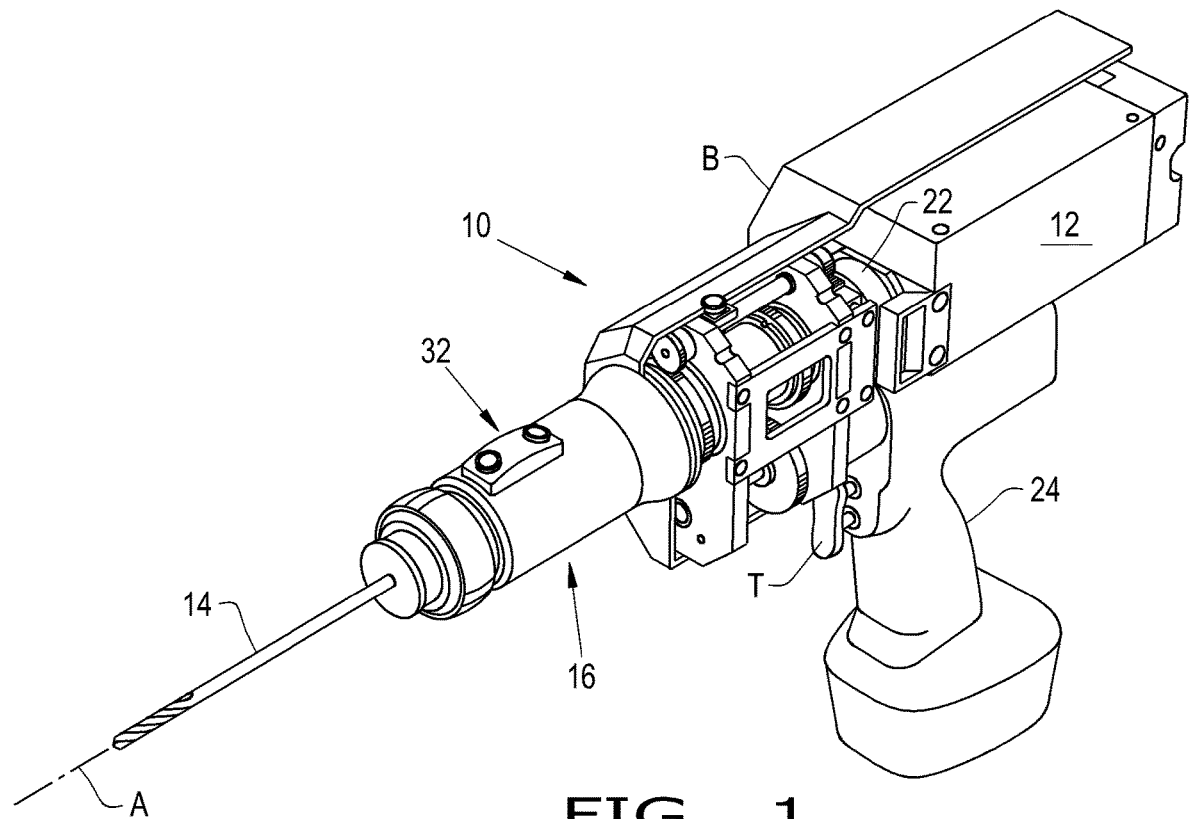
FIG. 1 is a perspective partially exposed view of the tool system of the present invention with the X-ray source in a centered position.

Referring to the drawings, and more particularly to FIGS. 1-6, there is illustrated a surgical viewing system 10, such as a tool assembly 10, in the form of a drill 10 having an X-ray source 12 that can be moved or shifted with respect to a drill bit 14 by the rotation of a forward handle 16. Although, the illustrations include a drill bit 14 and tool 10 is often referred to as a drill 10, tool assembly 10 can perform other rotational tasks, such as the installation of screws or other rotational uses in surgery.

Figure 2:
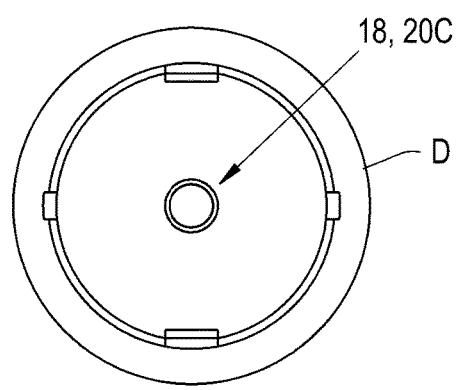
FIG. 2 is an image displayed on a display with the X-ray source of the drill of FIG. 1 in a centered position.
Figure 3:
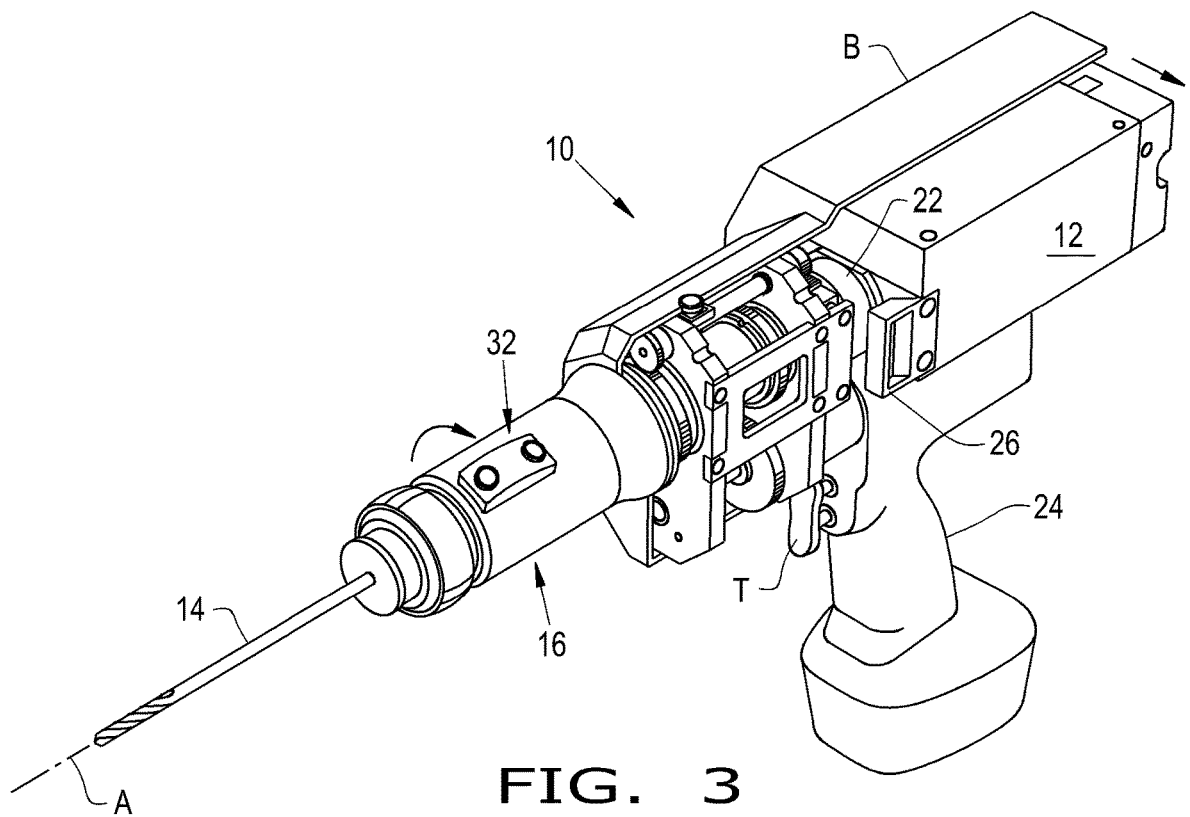
FIG. 3 is an illustration of the drill of FIG. 1 with the X-ray source in a left-shifted position.
Figure 4:
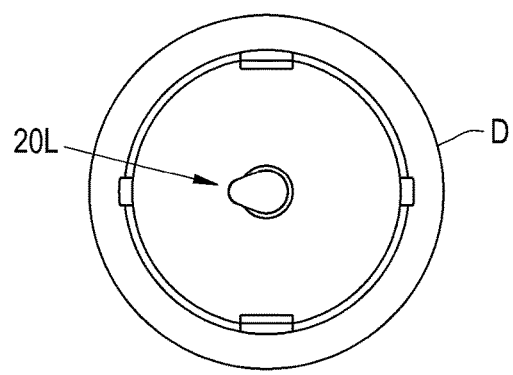
FIG. 4 is an image displayed on a display with the X-ray source of the drill of FIG. 3 in a left-shifted position.
Figure 5:
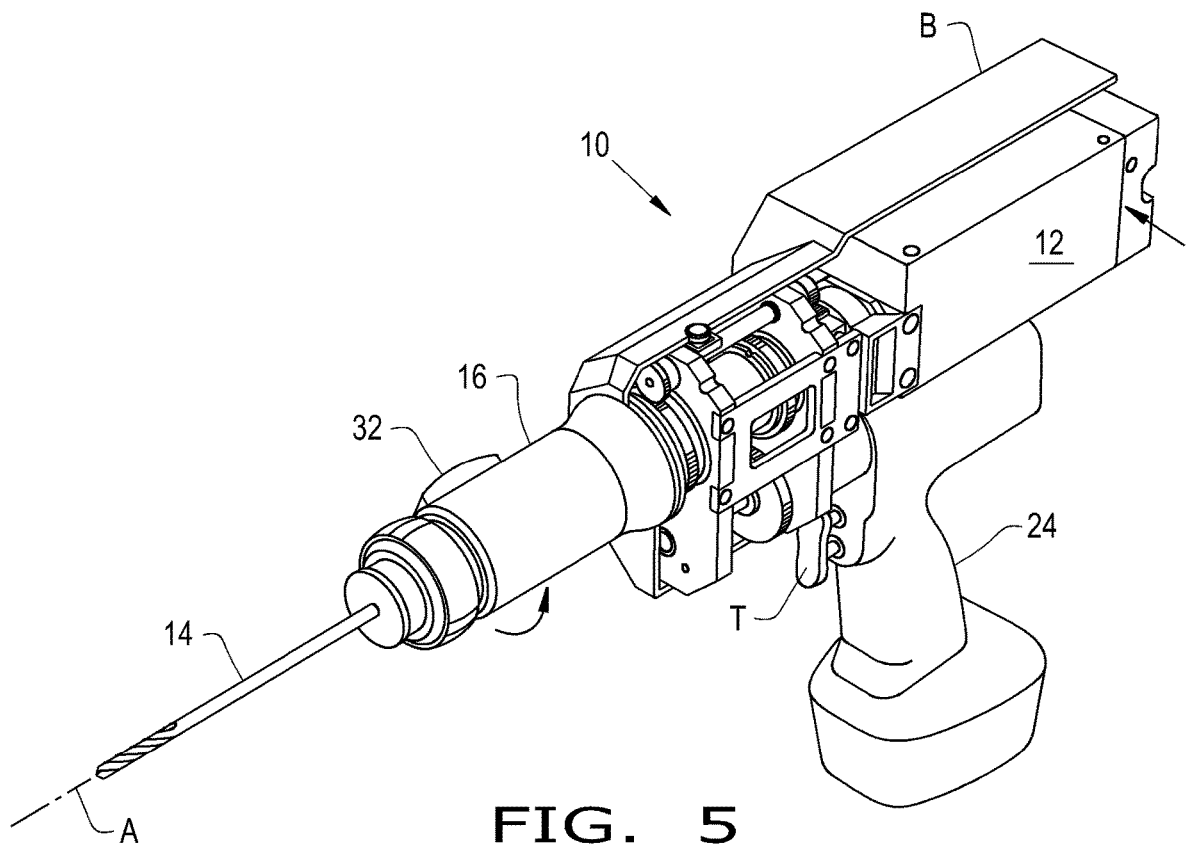
FIG. 5 is an illustration of the drill of FIGS. 1 and 3 with the X-ray source in a right-shifted position.
Figure 6:
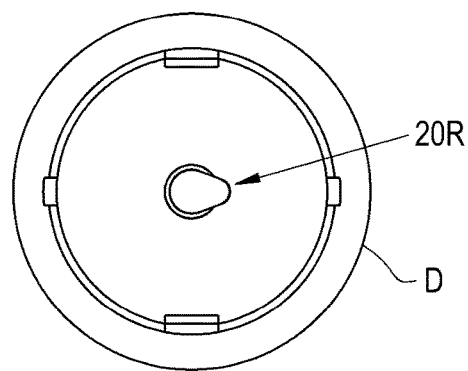
FIG. 6 is an image displayed on a display with the X-ray source of the drill of FIG. 5 in the right-shifted position.
Figure 7:
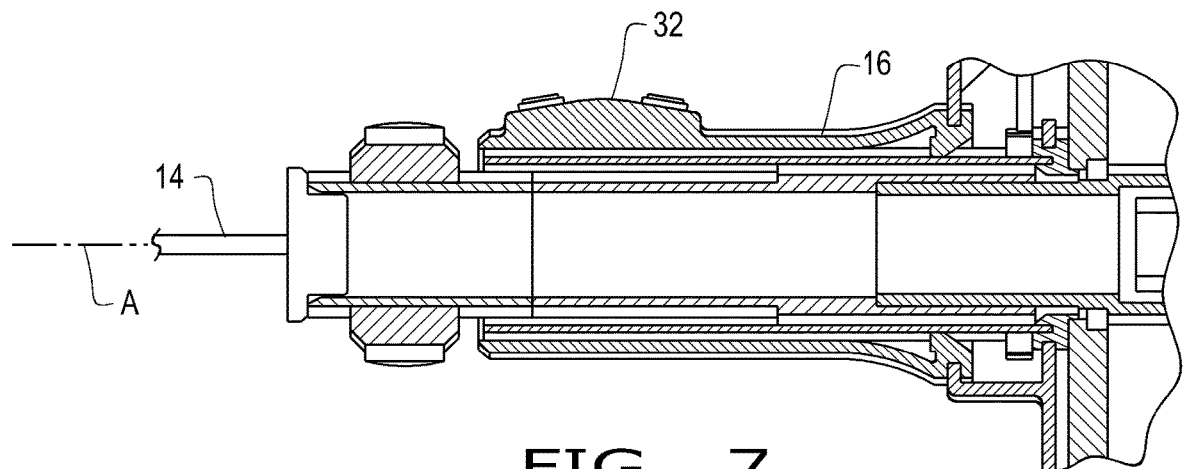
FIG. 7 is a side cross-sectional view of a forward handle and spindle of the drill of FIGS. 1, 3 and 5.

An X-ray source focal spot 18 can be moved left or right behind drill bit 14, which is done by moving the entire removable X-ray source module 12. When source 12 is shifted to the side, the image looks like the viewer is looking down the side of the bit, as illustrated in FIGS. 2, 4 and 6. In FIG. 2 the source is centered, or coaxial with drill bit 14, which is viewed on a display D as a central circular representation 20C. In FIG. 4 the source is left shifted relative to drill bit 14 so that the image is viewed as looking along the left side of drill bit 14 with a shifted image 20L of bit 14. In FIG. 6 the source is right shifted relative to drill bit 14 so that the image is viewed as looking along the right side of drill bit 14 with a shifted image 20R of drill bit 14. By viewing the images 20C, 20L, 20R with the source in the left, center and/or right positions, the user can easily judge whether or not drill bit 14 is aimed at the center of the target for a hole. While in the illustrated embodiment the movement of X-ray source 12 is left/right, other directions are also contemplated, such as up/down or any other combination of positions which provides the perspective of in the visual image of the tip of drill bit 14 relative to the target hole.

An actuator 16, shown as a forward handle 16 in the form of a handgrip 16 is used to actuate the movement of X-ray source 12, by twisting handgrip 16 about an axis A. A linkage system between hand grip 16 and X-ray source 12 causes the shifting of source 12. The linkage system can be in the form of a gear train so that X-ray source module 12 is moved by twisting hand grip 16 to the right (clockwise about axis A as viewed from the operator's perspective) and to the left (counterclockwise about axis A as viewed from the operator's perspective) to effect the right and left shifting.

The installed X-ray source module 12 clips firmly into a collimator member 22 such that the entire module 12 is translated when collimator member 22 is moved. Twistable handgrip 16 allows the surgeon to keep one hand on handle 24 of drill 10 and stabilize the forward portion of the assembly with the other hand on handgrip 16, while still allowing the first hand to control the drill and the second hand to control the X-ray source focus spot movement, all at the same time. Being able to change the position of X-ray source 12 while guiding drill bit 14 provides the user with increased visibility and the ability to confirm the path of drill bit 14 as it is moved toward the target. Tool 10 rotates drill bit 14 about axis A and X-ray source 12 is moved relative to axis A such that X-ray source 12 can be positioned coaxial with axis A, or to one side or the other of axis A, while the X-ray beam emanating from source 12 remains parallel or substantially parallel to axis A (the movements of X-ray source 12 being perpendicular to axis A), so that the practice of the method of the present invention can be carried out. It is also contemplated that the collimator could be part of the X-ray source assembly, and the retention features could be part of tool assembly 10. One advantage of using this alternate construct is that the rest of the tool could be made disposable, eliminating reprocessing/sterilization issues.

Other embodiments to move the X-ray source 12 are also contemplated. The user could move a lever, turn a knob or rotate a wheel to move source 12. Actuator 16 could be positioned so that the user's hand that holds the surgical handpiece 24 (rotary power unit) could be used to move the source via a grip, knob or lever, without removing the hand from handpiece 24. This would free up the other hand for important tasks such as maintaining reduction of a bone fracture.

Furthermore, the movement of source 12 could be motorized. A small electric motor connected to a gear train (linear translator) could move collimator 22 and X-ray source 12 as an assembly. The electric motor could be controlled using buttons, either on the hand grip and/or in reach of the hand holding the handpiece.

It is further contemplated that a shifting of X-ray source 12 from side-to-side can be done by a dithering source 12 between two or more positions. The output of X-ray source 12 can be continuous, or it can be pulsed at each position to remove artifacts of movement. The resulting output images could be displayed without alteration or could be processed to show the scene in an optimal way, removing the "shadow" of the bit in each image to give a clearer image of the bit tip in relation to the hole or where the hole is targeted to be. The positions of the focal source could be in any pattern, such as triangle, square or any polygon. The movement of the focus spot could be actuated by a mechanical movement that physically moves the X-ray tube assembly. Or it could be moved electronically by applying a varying electric field to the X-ray tube.

Figure 8:
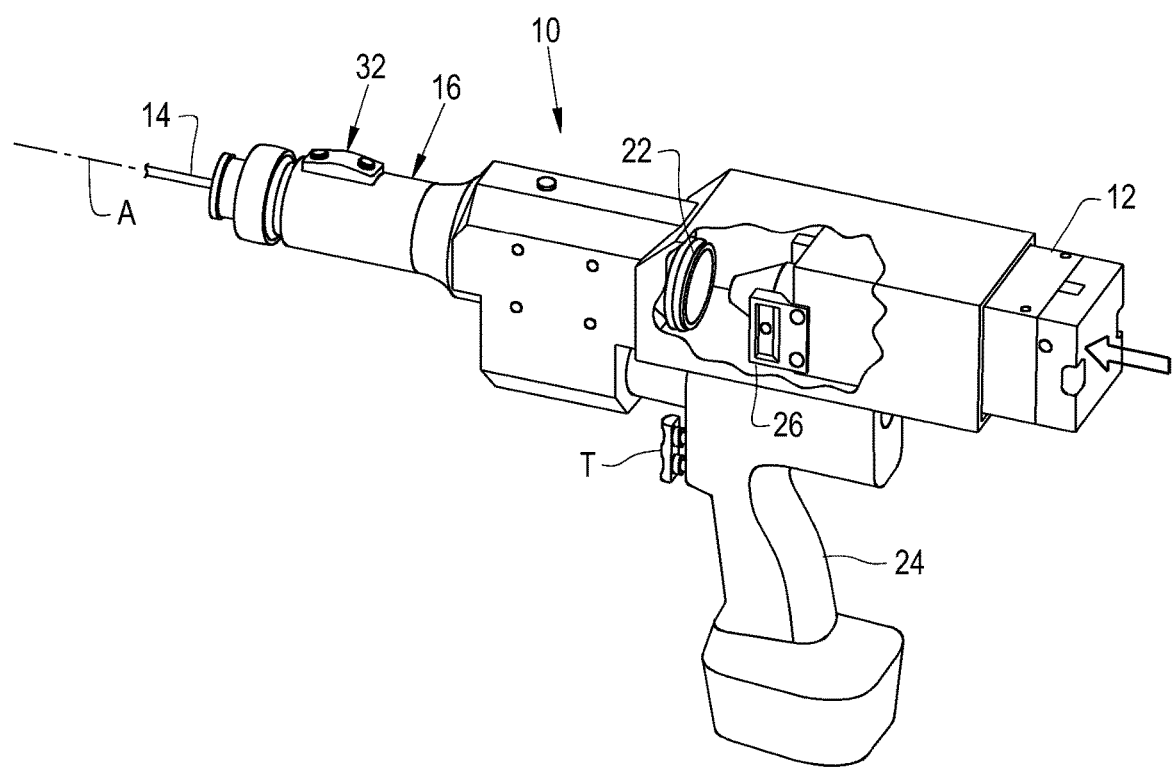
FIG. 8 is a partially sectioned view of the drill of FIGS. 1, 3 and 5, showing the insertion of the X-ray source.
Figure 9:
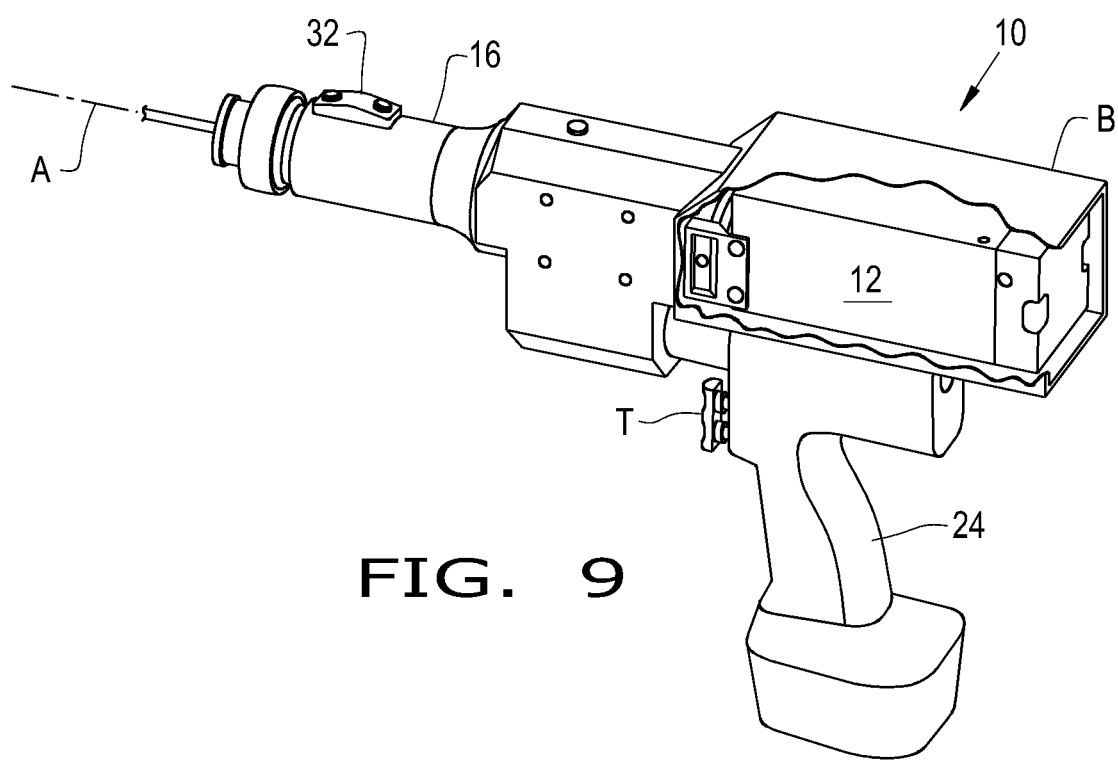
FIG. 9 is a partially sectioned view of the drill of FIGS. 1, 3, 5 and 8, showing the X-ray source fully inserted.

X-ray source 12 is a single removable module as illustrated in FIGS. 8 and 9, which respectively show X-ray source 12 being inserted into tool 10, and X-ray source 12 being fully engaged in tool 10. X-ray source module 12 contains an X-ray source component, electronics, a battery and a connector to a wiring harness. Several features of X-ray source module 12 are designed for it to be easily installed and removed from tool 10 to allow the drill attachment unit to be sterilized separately. The exterior of module 12 is designed such that it can be inserted and removed from the drill attachment via a smooth motion in one direction (opposite to the direction illustrated in FIG. 8).

Figure 10:
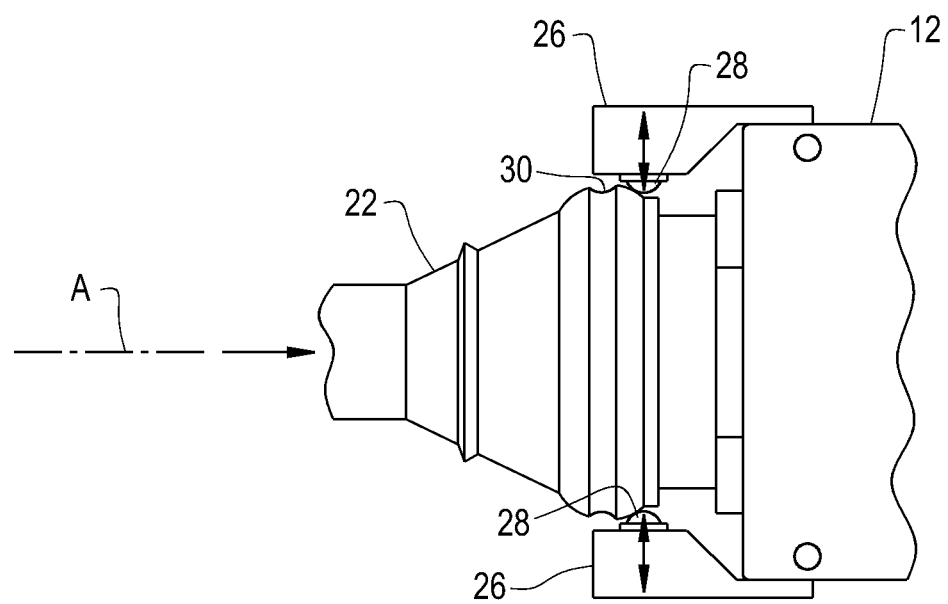
FIG. 10 is a side view of the interface between the collimator and the X-ray source of the drill of FIGS. 1, 3, 5, 8 and 9.
Figure 11A:
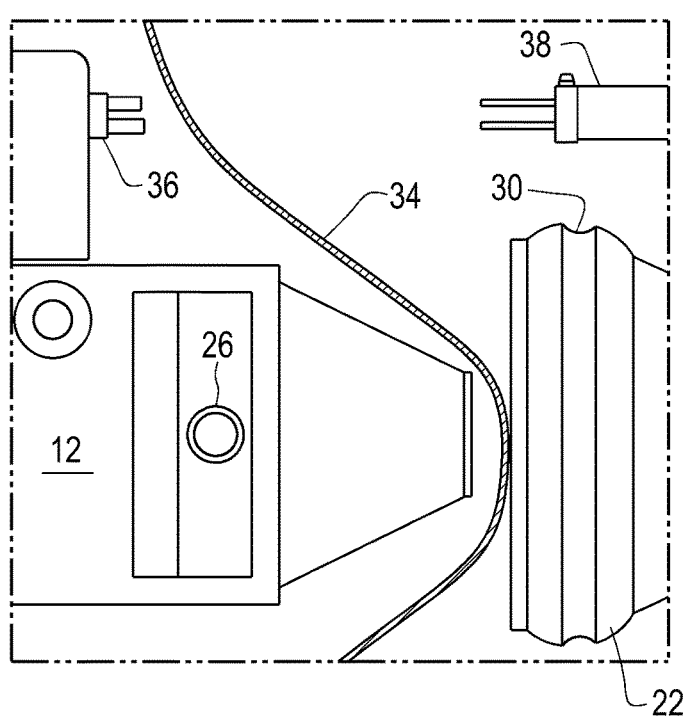
FIG. 11A is an internal view of the drill of FIGS. 1, 3, 5, 8 and 9 illustrating the insertion of the X-ray source with a sterile bag/barrier into the body of the drill as it is approaching the collimator.
Figure 11B:
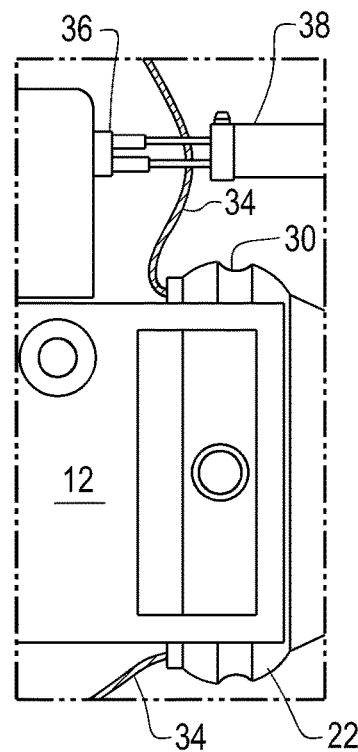
FIG. 11B is another internal view of the drill of FIGS. 1, 3, 5, 8 and 9 illustrating a sequential view to that of FIG. 11A with the insertion/mating of the X-ray source, having a sterile bag/barrier, to the collimator.

X-ray source 12 being a single removable module 12 is key to both moving the X-ray focal spot, and to making the system capable of being used within the sterile field of a surgical procedure. X-ray source 12 and collimator 22 have features for alignment and retention, as can be seen in FIGS. 10 and 11. FIGS. 11A and 11B are a two-part illustration of the same elements, with FIG. 11A illustrating the cone of X-ray source 12 approaching collimator 22 with bag 34 in an unpierced state. FIG. 11B shows these same components with X-ray source 12 being fully mated with collimator 22, with a portion of bag 34 being situated between X-ray source 12 and collimator 22, while pins from connector 38 have pierced bag 34 and connected with connector 36.

Retaining features 26 in the front of module 12 interface with collimator 22 to firmly clip source module 12 into position, allowing source 12 and collimator 22 to move as one unit. Retaining features 26 are illustrated as movable protrusions 28 that interact with groove 30 of collimator 22. As module 12 is inserted into collimator 22 retaining features 26 move outwardly and then rest in groove 30 to thereby couple X-ray source 12 to collimator 22.

Furthermore, the cone on the front of X-ray source 12 is a reference surface to locate the focal spot relative to collimator 22. Collimator 22 is conical and is complimentary, so as to match and mate to the cone of X-ray source 12, ensuring that the focus spot is as close to a center axis of collimator 22 and as near as possible to the optimal position along the center axis.

Having collimator 22 move with X-ray source 12 simplifies the collimator design and reduces the amount of material required, which reduces mass and cost. It also allows the shape of collimator 22 to conform closely to the shape of the nosecone of X-ray source 12, ensuring that stray ra/diation is minimized.

An X-ray source imaging mode is selected using a button assembly 32 on handgrip 16. System 10 can be used in a single shot or a live video mode, as selected with button assembly 32. The user can select the imaging mode using the two switches of button assembly 32 on handgrip 16. A single-shot imaging button commands X-ray source 12 to turn on and then off after a preselected exposure time has elapsed. The button also commands source module 12 to send information to system 10 indicating that a single image has been selected. System 10 then instructs an imager unit to acquire a single image for display on display D with the set exposure time and presents it to the user on display D.

When the live video mode button is pressed and held, X-ray source 12 turns on and remains on until the button is released. The imager unit sends a steady stream of images to the system for display on display D, until the intensity of X-ray signals falls below a pre-determined threshold, then X-ray source 12 is deactivated.

Imaging mode switches are also on the drill attachment body B, also known as housing B, close to a drill trigger T, on both sides, which can be reached by the hand that is operating tool 10, regardless of whether the user is using their left or right hand.

Other possible methods for controlling the imaging mode are via a surgeon-operated foot pedal switch and/or an audio sensor connected to a processor that recognizes voice commands.

X-ray source module 12 is enclosed in a bag 34 or a barrier 34 to maintain the sterile field. Steam sterilization (autoclaving) is the most common method of instrument sterilization in hospitals. However, X-ray source module 12 is not steam sterilizable because the lifetime and performance of the electronics and battery are easily degraded by high temperature and moisture. Before it is inserted into housing B of tool 10, X-ray source module 12 is enclosed in a sterile plastic bag 34 using an aseptic transfer procedure. The bagged module 12 is inserted into tool 10 and is secured in the correct position by pressing the module into the housing until the retainer features 26 hold X-ray source 12 in place relative to collimator 22. Plastic bag 34 is flexible and thin, such that it does not interfere with X-ray transmission or retaining features 26 of X-ray source 12.

A female electrical connector 36 of X-ray source 12 is contained within bag 34, and a male electrical connector 38 is part of drill attachment housing B. As connectors 36 and 38 are seated, the sharp male pins of connector 38 pierce through plastic bag 34 and contact the female receptacles of connector 36.

The electrical connection between X-ray module 12 and the wiring harness for buttons 32 is made when the male connector on the drill attachment housing punctures through the plastic and mates with female connector 36 of X-ray module 12. The sterility of tool 10 outside of module 12 is maintained because the connections are made completely inside the drill attachment housing B. Finally, the back of the drill attachment housing B is enclosed by installing a cap or closing a door on the housing B.

Collimator 22 is designed to minimize stray radiation, since collimator 22 surrounds the nose cone of X-ray source module 12. Collimator 22 is made of a tungsten heavy alloy (HA) to minimize transmission of X-rays. Tungsten HA is commonly used for X-ray shielding and is known in the X-ray imaging field. The thickness of each of collimator 22 features is chosen to minimize collimator mass while also minimizing stray radiation.

Figure 12A:
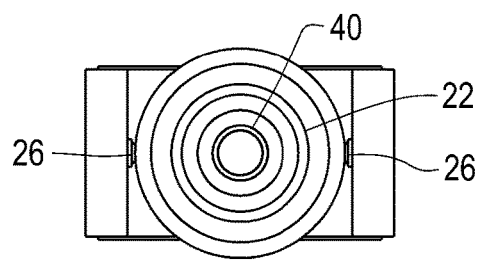
FIG. 12A is an end view of the collimator of FIGS. 10 and 11 illustrating a round geometry.
Figure 12B:
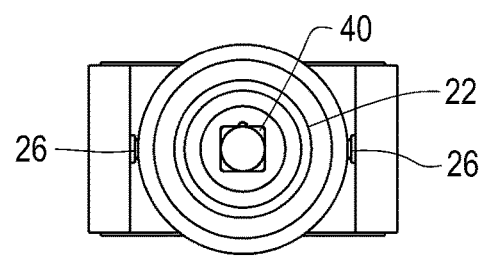
FIG. 12B is an end view of the collimator of FIGS. 10 and 11 illustrating a square geometry.
Figure 12C:
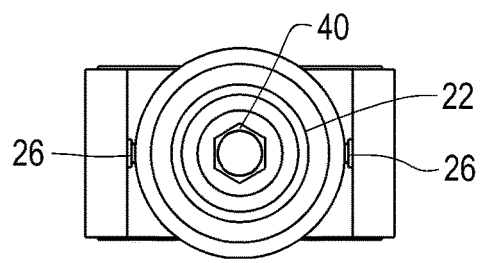
FIG. 12C is an end view of the collimator of FIGS. 10 and 11 illustrating a hexagonal geometry.

The perimeter shape of the beam falling on the imager is defined by a collimator aperture 40. The aperture shape is chosen to facilitate perspective distortion correction. The perspective distortion correction algorithm uses the expected shape of aperture 40 to correct the perspective distortion in the image. Many shapes of aperture 40 can be used, including round, square or any polygon, which is illustrated in FIGS. 12A-12C. shapes of aperture 40 include circular (FIG. 12A), square with a notch (FIG. 12B), and hexagonal (FIG. 12C).

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A surgical viewing system, comprising:
an X-ray source creating a beam of radiation;
a surgical tool with the X-ray source coupled thereto, the surgical tool having an axis of rotation; and
an actuator including a handgrip coupled to the surgical tool causing the beam of radiation to be shifted relative to the axis of rotation.

2. The viewing system of claim 1, wherein the shifting of the beam of radiation is such that the beam of radiation remains parallel with the axis of rotation as the beam of radiation is shifted.

3. The viewing system of claim 1, wherein the actuator causes the X-ray source to move in directions perpendicular to the axis of rotation.

4. The viewing system of claim 3, wherein the handgrip is rotated to shift the beam of radiation relative to the axis of rotation.

5. The viewing system of claim 4, wherein the handgrip is generally coaxial with the axis of rotation.

6. The viewing system of claim 5, wherein the handgrip is rotatable in a clockwise direction causing the X-ray source to shift in a first direction relative to the axis of rotation, and the handgrip is rotatable in a counterclockwise direction causing the X-ray source to shift in a second direction opposite of the first direction.

7. The viewing system of claim 1, further comprising a collimator coupled to the X-ray source, the collimator being coupled to the actuator.

8. The viewing system of claim 7, wherein the collimator has a geometrically shaped aperture, the geometrical shape being used in an image correction algorithm to alter an image produced by the viewing system.

9. The viewing system of claim 7, wherein the collimator and/or the X-ray source has retaining features that hold the collimator and the X-ray source to each other in a coupled state.

10. The viewing system of claim 9, wherein the X-ray source is enclosed by a bag prior to being coupled to the collimator.

11. The viewing system of claim 10, wherein the bag is pierced by at least one electrical connector as the X-ray source is coupled to the collimator.

12. A surgical tool, comprising:
a housing;
an X-ray source positioned within the housing, the X-ray source creating a beam of radiation, the surgical tool having an axis of rotation; and
an actuator coupled to the surgical tool causing the beam of radiation to be shifted relative to the axis of rotation, wherein the actuator includes a handgrip.

13. The surgical tool of claim 12, wherein the shifting of the beam of radiation is such that the beam of radiation remains parallel with the axis of rotation as the beam of radiation is shifted.

14. The surgical tool of claim 12, wherein the actuator causes the X-ray source to move in directions perpendicular to the axis of rotation.

15. The surgical tool of claim 14, wherein the handgrip includes a button assembly.

16. The surgical tool of claim 15, wherein the handgrip is generally coaxial with the axis of rotation.

17. The surgical tool of claim 16, wherein the handgrip is rotatable in a clockwise direction causing the X-ray source to shift in a first direction relative to the axis of rotation, and the handgrip is rotatable in a counterclockwise direction causing the X-ray source to shift in a second direction opposite of the first direction.

18. The surgical tool of claim 12, further comprising a collimator coupled to the X-ray source, the collimator being coupled to the actuator.

19. The surgical tool of claim 18, wherein the collimator has a geometrically shaped aperture, the geometrical shape being used in an image correction algorithm to alter an image produced by the surgical tool.

20. The surgical tool of claim 18, wherein the collimator and/or the X-ray source has retaining features that hold the collimator and the X-ray source to each other in a coupled state.

* * * * *